(12) United States Patent
Frecker et al.

(10) Patent No.: US 8,382,791 B2
(45) Date of Patent: Feb. 26, 2013

(54) SURGICAL TOOL

(75) Inventors: Mary Frecker, State College, PA (US);
Abraham Mathew, Hershey, PA (US);
Eric Pauli, Hummelstown, PA (US);
Andrew Rau, Jackson Center, PA (US);
Jeffrey Kingston, Bronx, NY (US);
Greg Hayes, Pipersville, PA (US);
Andrew Baranak, Chalfont, PA (US)

(73) Assignee: The Penn State Research Foundation, University Park, PA (US)

( * ) Notice: Subject to any disclaimer, the term of this patent is extended or adjusted under 35 U.S.C. 154(b) by 243 days.

(21) Appl. No.: 12/871,318

(22) Filed: Aug. 30, 2010

(65) Prior Publication Data

US 2011/0112568 A1      May 12, 2011

Related U.S. Application Data

(60) Provisional application No. 61/237,954, filed on Aug. 28, 2009.

(51) Int. Cl.
*A61B 17/00* (2006.01)

(52) U.S. Cl. ........................................ 606/205

(58) Field of Classification Search .......... 606/205–208, 606/1, 51, 52; 600/104
See application file for complete search history.

(56) References Cited

U.S. PATENT DOCUMENTS

| | | | |
|---|---|---|---|
| 5,122,130 A | 6/1992 | Keller | |
| 5,154,721 A | 10/1992 | Perez et al. | |
| 5,211,655 A | 5/1993 | Hasson | |
| 5,269,804 A | 12/1993 | Bales et al. | |
| 5,284,487 A | 2/1994 | Hartmeister | |
| 5,368,596 A | 11/1994 | Burkhart | |
| 5,395,364 A * | 3/1995 | Anderhub et al. | 606/51 |
| 5,441,494 A | 8/1995 | Ortiz | |
| 5,474,571 A | 12/1995 | Lang | |
| 5,558,100 A * | 9/1996 | Cox | 600/564 |
| 5,562,702 A | 10/1996 | Huitema et al. | |
| 5,713,919 A | 2/1998 | Lahr | |
| 5,810,876 A * | 9/1998 | Kelleher | 606/205 |
| 5,827,281 A * | 10/1998 | Levin | 606/51 |
| 5,865,724 A * | 2/1999 | Palmer et al. | 600/104 |
| 5,897,507 A | 4/1999 | Kortenbach et al. | |
| 5,908,437 A * | 6/1999 | Asano et al. | 606/205 |
| 6,358,249 B1 | 3/2002 | Chen et al. | |
| 6,361,534 B1 | 3/2002 | Chen et al. | |
| 6,364,879 B1 * | 4/2002 | Chen et al. | 606/45 |
| 6,425,896 B1 * | 7/2002 | Baltschun et al. | 606/51 |
| 6,544,194 B1 | 4/2003 | Kortenbach et al. | |
| 6,767,349 B2 * | 7/2004 | Ouchi | 606/51 |
| 6,964,662 B2 | 11/2005 | Kidooka | |
| 7,189,234 B2 | 3/2007 | Zucherman et al. | |

(Continued)

OTHER PUBLICATIONS

Rau, A. et al., Design of a multifunctional forceps for use in endoscopic surgery, *Proceedings of the 2010 Design of Medical Devices Conference*, Minneapolis, MN, Apr. 13-15, 2010.

(Continued)

*Primary Examiner* — Gary Jackson
*Assistant Examiner* — Amy Shipley
(74) *Attorney, Agent, or Firm* — Gifford, Krass, Sprinkle, Anderson & Citkowski, P.C.

(57) ABSTRACT

Recent advances in minimally invasive surgical procedures have created a demand for smaller scale tools with improved performance characteristics. Attempts to scale down modern tools to the meso level (1-5 mm) have caused severe performance losses. Surgical tools of the present invention provide significant improvements in operable range and force application for both grasping and spreading when compared to currently used endoscopic forceps. This is achieved by using two actuators that separately control the spreading and grasping functions of the surgical tool.

11 Claims, 4 Drawing Sheets

U.S. PATENT DOCUMENTS

| | | | | |
|---|---|---|---|---|
| 7,326,209 | B2 * | 2/2008 | Kidooka | 606/51 |
| 7,927,327 | B2 * | 4/2011 | Lu et al. | 606/1 |
| 2002/0111621 | A1 | 8/2002 | Wallace et al. | |
| 2005/0090817 | A1 * | 4/2005 | Phan | 606/41 |

OTHER PUBLICATIONS

Rau, A. et al., Design of a multifunctional tissue grasper and spreader for use in incisionless surgery. Presented at the SME 2009 International Design Engineering Technical Conferences, ASME Student Mechanism and Robot Design Competition—Graduate Level Mechanisms Division, San Diego, CA, Sep. 1, 2009.

East Coast Endoscopy. Fork Jaw Retriever. http://endoscopyforceps.com/. Accessed on Dec. 29, 2011 and believed to have been available as early as Jul. 2010.

Boston Scientific. Graspit® Nitinol Stone Retrieval Forceps. www.bostonscientific.com. Accessed on Dec. 7, 2011 and believed to have been available as early as Jul. 2010.

Melzer, Stoeckel. The Use of NiTi Alloys for Surgical Instruments. Materialls in Clinical Applications. (ed.) P. Vincenzini, Techna Srl. 1995.

Stryker. MiniLap Grasper. www.stryker.com. Accessed on Dec. 7, 2011 and believed to have been available as early as Jul. 2010.

Olympus. Grasping Forceps FG-4L-1. www.olympusamerica.com. Accessed on Dec. 29, 2011 and believed to have been available as early as Jul. 2010.

Boston Scientific. Radial Jaw 3. www.bostonscientific.com. Accessed on Dec. 29, 2011 and believed to have been available as early as Jul. 2010.

Olympus. Biopsy Forceps. www.olympusamerica.com. Accessed on Dec. 29, 2011 and believed to have been available as early as Jul. 2010.

Olympus. Rat Tooth Alligator Jaw. www.olympusamerica.com. Accessed on Dec. 29, 2011 and believed to have been available as early as Jul. 2010.

Boston Scientific. SpyBite® Biopsy Forceps. www.bostonscientific.com. Accessed on Dec. 29, 2011 and believed to have been available as early as Jul. 2010.

http://www.eisnerusa.com/products.cfm?sub=NEUROENDOSCOPY. Eisner USA, LLC. Biopsy Forceps. Image accessed in Jul. 2010.

* cited by examiner

SURGICAL TOOL

REFERENCE TO RELATED APPLICATION

This application claims priority to U.S. Provisional Patent Application Ser. No. 61/237,954, filed Aug. 28, 2009, the entire content of which is incorporated herein by reference.

FIELD OF THE INVENTION

The present invention relates generally to surgical tools for use in endoscopic procedures. In specific embodiments, multifunctional surgical tools for use in endoscopic procedures are described.

BACKGROUND OF THE INVENTION

Demand for surgical procedures which drastically reduce patient recovery time and discomfort has led to a paradigm shift in modern medicine. Minimally invasive surgery (MIS) is a rapidly developing medical practice and is constantly being advanced through the introduction of novel experimental procedures. MIS procedures require smaller external incisions than traditional surgery, or are completely devoid of external incisions. The benefits of such procedures from a patient care perspective include less discomfort and scaring, shortened recovery time and decreased chance of surgical infections. These benefits have caused an extremely high demand for MIS over traditional surgery, resulting in the introduction of several groundbreaking procedures.

The scope of endoscopic therapy for diseases has significantly broadened with the use of techniques allowing dissection of the layers of the stomach and selective removal of superficial layers. Several previously open surgical procedures can now be accomplished through minimally invasive endoscopic procedures. Furthering of this field requires tools adapted for flexible endoscopic application.

A procedure known as natural orifice transluminal endoscopic surgery (NOTES) is particularly promising as a minimally invasive technique. During NOTES, the surgeon passes a flexible endoscope through a natural orifice, e.g. the mouth or anus, in order to access an internal surgical site.

A novel NOTES procedure for transgastric access is currently under development. During this experimental procedure, the endoscope is inserted through the esophagus and a small internal incision is made in the inner lining of the stomach. The surgeon then passes a forceps tool through the endoscope and tunnels between the layers of the stomach wall, subsequently making a second incision in the outer layer of the stomach. Tunneling between the layers of the stomach wall creates an effective seal between the acidic inside of the stomach and the abdominal cavity, preventing unwanted leakage. After the procedure has concluded, no external incisions are present, and the internal incisions are sutured.

The tunneling procedures and dissection of tissue using millimeter scale has proven to be extremely tedious using modern endoscopic tools. At small scales, such as 1-5 mm diameter or less, current tool designs are not capable of applying large spreading forces, thereby greatly impeding the ability to separate and dissect tissue. Dissection of tissue is key in any surgery and irrespective of the location and minimally invasive technique, small tools capable of tissue dissection and separation, that pass through the small channels of the current and envisioned endoscopes and other surgical devices are needed. Without these minimally invasive and NOTES procedures cannot to develop and advance effectively.

There is presently a dearth of multifunctional surgical tools for use in endoscopy. Exchanging the tool tip at the distal end of an endoscope is not only tedious but also undesirably extends the length of a surgical procedure. There is a continuing need for multifunctional surgical tools for use in endoscopy.

SUMMARY OF THE INVENTION

Surgical tools are provided according to embodiments of the present invention which include a first elongated member and a second elongated member, each of the first and second elongated members having a proximal end, a distal jaw end, the first and second elongated members pivotally attached at a pivotal attachment, each of the first and second elongated members having a first actuator connection disposed between the proximal end and the pivotal attachment and a second actuator connection disposed between the distal end and the pivotal attachment; a pair of first actuators, one of the pair of first actuators connected to the first actuator connection of the first elongated member and the second of the pair of first actuators connected to the first actuator connection of the second elongated member; a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members to bring the distal jaw ends closer together and activation of the pair of second actuators urges pivotal movement of the first and second elongated members to move the distal jaw ends apart; and a housing supporting the pivotally attached elongated members.

Surgical tools are provided according to embodiments of the present invention which include a first elongated member and a second elongated member, each of the first and second elongated members having a proximal end, a distal jaw end, the first and second elongated members pivotally attached at a pivotal attachment, each of the first and second elongated members having a first actuator connection disposed between the proximal end and the pivotal attachment and a second actuator connection disposed between the distal end and the pivotal attachment; a pair of first actuators, one of the pair of first actuators connected to the first actuator connection of the first elongated member and the second of the pair of first actuators connected to the first actuator connection of the second elongated member; a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members to bring the distal jaw ends closer together and activation of the pair of second actuators urges pivotal movement of the first and second elongated members to move the distal jaw ends apart; a housing supporting the pivotally attached elongated members and a flexible or non-flexible tool shaft attached to the housing supporting the pivotally attached elongated members.

A controller in operable connection with the pair of first actuators and/or the pair of second actuators is included according to embodiments of surgical tools of the present invention A wire in electrical communication with a power source and with the distal jaw end of at least one of the first and second elongated members, the power source operable to deliver an electrical current via the wire to the distal jaw end of at least one of the first and second elongated members. Delivery of the electrical current to the distal jaw end of at least one of the first and second elongated members is useful, for example, to cauterize a tissue.

Optionally, an included tool shaft is an articulated tool shaft.

Surgical tools according to embodiments of the present invention are provided that include a housing having a first connecting pin opening and a second connecting pin opening; a first elongated member and a second elongated member, each of the first and second elongated members having a proximal end, a distal jaw end and a connecting pin opening disposed therebetween for pivotal attachment of the first and second elongated members, each of the first and second elongated members having a first actuator connection disposed between the proximal end and the connecting pin opening and a second actuator connection disposed between the distal end and the connecting pin opening; a connecting pin attaching the first elongated member, second elongated member and the housing; a pair of first actuators, one of the pair of first actuators connected to the first actuator connection of the first elongated member and the second of the pair of first actuators connected to the first actuator connection of the second elongated member; and a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members to bring the distal jaw ends closer together and activation of the pair of second actuators urges pivotal movement of the first and second elongated members to move the distal jaw ends apart.

Surgical tools according to embodiments of the present invention are provided that include a housing having a first connecting pin opening and a second connecting pin opening; a first elongated member and a second elongated member, each of the first and second elongated members having a proximal end, a distal jaw end and a connecting pin opening disposed therebetween for pivotal attachment of the first and second elongated members, each of the first and second elongated members having a first actuator connection disposed between the proximal end and the connecting pin opening and a second actuator connection disposed between the distal end and the connecting pin opening; a connecting pin attaching the first elongated member, second elongated member and the housing; a pair of first actuators, one of the pair of first actuators connected to the first actuator connection of the first elongated member and the second of the pair of first actuators connected to the first actuator connection of the second elongated member; and a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members to bring the distal jaw ends closer together and activation of the pair of second actuators urges pivotal movement of the first and second elongated members to move the distal jaw ends apart, wherein the housing is attached to a distal functional end of a flexible insertion portion of an endoscopic instrument and/or to a flexible sheath of a flexible insertion portion of an endoscope.

Methods are provided according to embodiments of the present invention which include providing a surgical tool described herein, inserting the surgical tool into the body of a surgical patient; and activating the first pair of actuators to grasp a tissue of the surgical patient and/or activating the second pair of actuators to spread a tissue of the surgical patient.

Methods are provided according to embodiments of the present invention which include providing a surgical tool described herein, inserting the surgical tool into the body of a surgical patient; and activating the first pair of actuators to grasp a tissue of the surgical patient and/or activating the second pair of actuators to spread a tissue of the surgical patient, and delivering and electrical current to the distal jaw end of at least one of the first and second elongated members in contact with a tissue of the surgical patient, thereby cauterizing the tissue of the surgical patient.

DETAILED DESCRIPTION OF THE INVENTION

A multifunctional grasper/spreader surgical tool which can be used via minimally invasive surgery platforms like endoscopes, including laparoscopes etc, such as through the working channel of endoscopes, and which can apply appreciable grasping and spreading forces to tissue is provided according to embodiments of the present invention.

Flexible endoscopes are generally characterized by an elongated flexible insertion portion which can be inserted into a patient's body. The elongated flexible insertion portion generally includes a functional distal end, for instance having an attached imaging device and/or surgical tool and a controller disposed at the proximal end of the elongated flexible insertion portion for control of the functional distal end by a user.

A multifunctional grasper/spreader surgical tool, referred to as a "surgical tool" herein according to embodiments of the present invention includes a housing and two mating jaws supported in the housing.

According to embodiments of the present invention, the surgical tool includes two pivotally connected elongate members, each having a distally located mating jaw. Any of various pivotal connectors can be used to pivotally connect the elongate members, exemplified by, but not limited to, a pivot pin or compliant mechanism.

An actuation mechanism for opening and closing the two mating jaws to perform tissue grasping and spreading functions of the surgical tool is included. Prior art forceps designs include a single set of 2 wires which control both the opening and closing of the forceps, resulting in very poor mechanical advantage in one loading direction. In contrast, according to embodiments of the present invention, the actuation mechanism includes a first actuator for opening the jaws to accomplish a tissue spreading function of the surgical tool and a second actuator to close the jaws and accomplish a tissue grasping function of the surgical tool.

Actuators for opening and closing the two mating jaws can include any actuator capable of urging movement of the two mating jaws. Exemplary actuators include, but are not limited to, wires. The terms "wire" and "wires" as used herein encompass single strands, multiple entwined strands, rods, cables.

Actuators can be made of materials compatible with surgical use, including but not limited to, metals such as stainless steel or plastics such as polytetrafluoroethylene. Actuators are operably connected to an endoscope handle or controller which allows a user to activate the actuators and control the opening and closing of the mated jaws.

According to embodiments of the present invention, mechanically controlled wire-actuators are included. Embodiments of a surgical tool of the present invention incorporate as a first actuator a first set of actuating wires for opening the mating jaws of the tool and a second set of actuating wires for closing the mating jaws of the tool as a second actuator.

The pivotally connected elongate members having distally located mating jaws are supported in a housing. The elongate members are pivotally attached to the housing by any of various pivotal connectors, exemplified by, but not limited to, a pivot pin or compliant mechanism. The housing is adapted to allow for opening and closing of the mating jaws and movement of the elongate members.

As noted above, a surgical tool according to embodiments of the present invention is useful in conjunction with an endoscope in performing endoscopic surgery. As is well-known, endoscopes for use in surgical procedures typically have several channels including light transmission, image transmission, air and water, and one or more "working channels" through which surgical instruments are inserted.

A surgical tool of the present invention can be reversibly or permanently attached to a tool shaft which supports the surgical tool. The tool shaft can be flexible or rigid depending on the intended application. In endoscope embodiments, the tool shaft is flexible and extends through the working channel of the endoscope. The housing of an inventive surgical tool optionally includes a connector adapted to reversibly attach the housing to the tool shaft.

The housing optionally includes a base having a channel therethrough such that actuators attached to the elongate members and operably connected to the endoscope handle or controller are disposed in the channel. The tool shaft may be hollow such that actuators can be disposed in the tool shaft.

Optionally, at least a portion of the tool shaft is articulated to allow for flexible and/or directed movement of the surgical tool at the distal end of the endoscope.

In a further option, a surgical tool according to embodiments of the present invention is in electrical communication with a power source to provide electrocautery functionality to the surgical tool.

Figure 1:
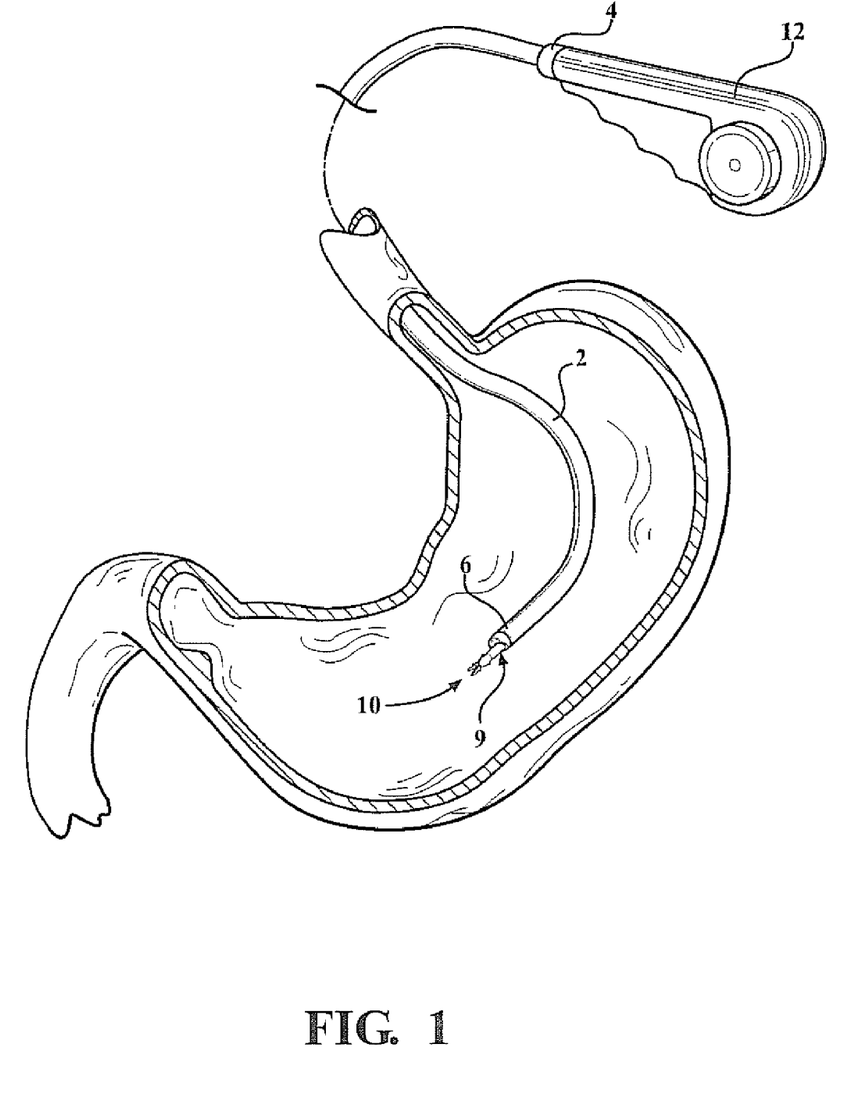
FIG. 1 is a perspective view of a surgical tool according to an embodiment of the present invention disposed through an endoscope, with the endoscope extending into the stomach of a surgical patient.

FIG. 1 shows an endoscope including a surgical tool of the present invention, 2. The endoscope extends between two ends 4 and 6 with the end 6 inserted into the body of a subject. The illustrated endoscope includes a handle or control, such as shown at 12, which is operably connected to an embodiment of a surgical tool of the present invention, 10. Surgical tool 10 is shown attached to a shaft 9.

Figure 2:
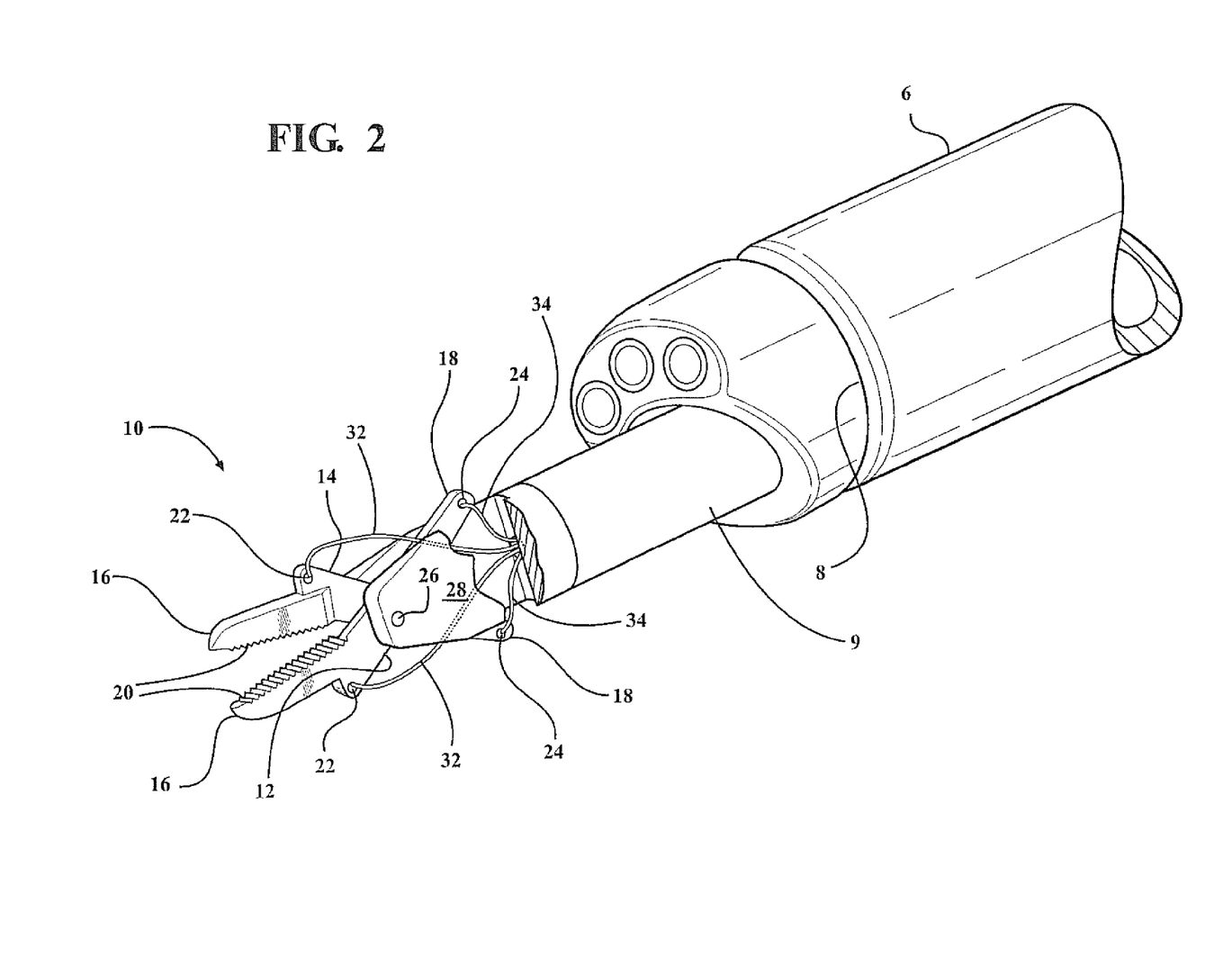
FIG. 2 is a perspective view of a surgical tool according to an embodiment of the present invention extending from the end of an endoscope.

A detailed view of the end 6 is provided in FIG. 2. As shown, the endoscope has a working channel 8 defined therethrough. Typically, this channel has a diameter in the range of 0.5 to 6 millimeters, and the diameter can be smaller or larger depending on the application.

FIG. 2 shows an embodiment of a surgical tool of the present invention, 10 attached to a shaft 9 which is removably disposed in working channel 8 of the endoscope. The illustrated surgical tool includes a first elongated member 12 and a second elongated member 14. Each of the first and second elongated members have a distal jaw end 16 and a proximal end 18. The lower sections of the elongated members incorporate an offset design to enable mating of the gripping surfaces of the jaws 20. The upper sections of the elongated members are stepped up and tapered to provide grasping/spreading areas and prevent tissue puncturing.

The first and second elongated members 12 and 14 are pivotally attached in an embodiment shown in FIG. 2. Each of the first and second elongated members 12 and 14 has a connecting pin opening disposed between the distal jaw end 16 and the proximal end 18 for insertion of a connecting pin therethrough. A connecting pin 26 pivotally attaching the first and second elongated members 12 and 14 to each other and to a housing 28 is illustrated.

Each of the first and second elongated members 12 and 14 has a first actuator connection 22 disposed between the distal jaw end 16 and the connecting pin opening and a second actuator connection 24 disposed between the proximal end 18 and the connecting pin opening.

A pair of first actuators 32 is shown. One of the pair of first actuators 32 is connected to the first actuator connection 22 of the first elongated member 12 and the second of the pair of first actuators 32 is connected to the first actuator connection 22 of the second elongated member 14. A pair of second actuators 34 is illustrated. One of the pair of second actuators 34 is connected to the second actuator connection 24 of the first elongated member 12 and the second of the pair of second actuators 34 is connected to the second actuator connection 24 of the second elongated member 14. Activation of the pair of first actuators 32 urges pivotal movement of the first and second elongated members 12 and 14 to bring the distal jaw ends 16 closer together to provide the tissue grasping function. Activation of the pair of second actuators 34 urges pivotal movement of the first and second elongated members 12 and 14 to move the distal jaw ends 16 apart, providing the tissue spreading function.

Figure 3:
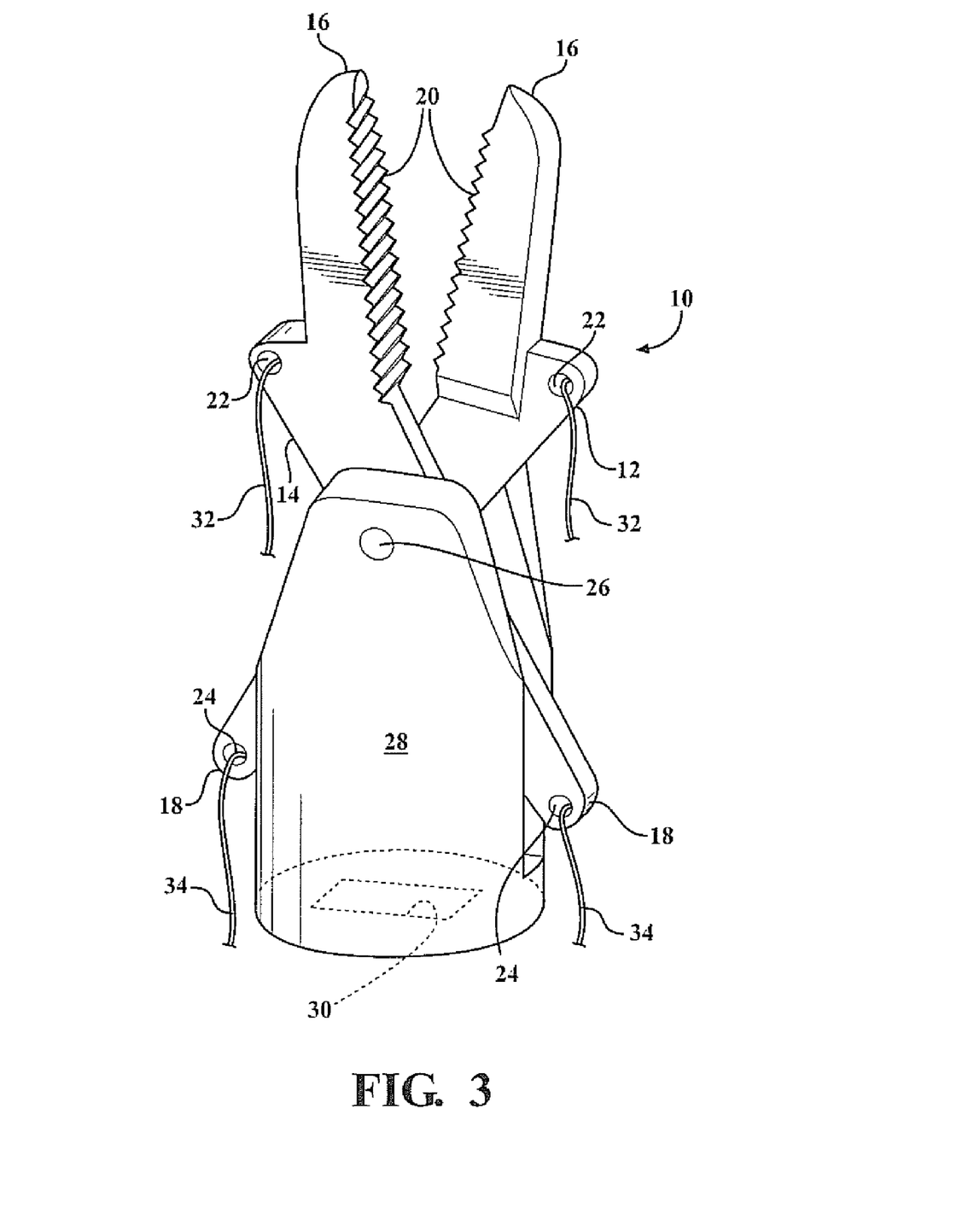
FIG. 3 is a perspective view of a surgical tool according to an embodiment of the present invention.

FIG. 3 shows an embodiment of a surgical tool of the present invention, 10. The illustrated surgical tool includes a first elongated member 12 and a second elongated member 14. Each of the first and second elongated members have a distal jaw end 16 and a proximal end 18.

Each of the first and second elongated members 12 and 14 has a connecting pin opening disposed between the distal jaw end 16 and the proximal end 18 for insertion of a connecting pin therethrough. A connecting pin 26 pivotally attaching the first and second elongated members 12 and 14 to each other and to a housing 28 is illustrated.

Housing 28 includes a channel 30 for reversible attachment of the housing 28 to a tool shaft. Optionally actuators 32 and 34 are disposed in the channel.

Each of the first and second elongated members 12 and 14 has a first actuator connection 22 disposed between the distal jaw end 16 and the connecting pin opening and a second actuator connection 24 disposed between the proximal end 18 and the connecting pin opening.

Actuators attached at first actuator connections 22 and second actuator connections 24 can be any actuator capable of urging movement of the attached distal jaw ends of the first and second elongated members.

A pair of first actuators 32 is shown in FIG. 3. One of the pair of first actuators 32 is connected to the first actuator connection 22 of the first elongated member 12 and the second of the pair of first actuators 32 is connected to the first actuator connection 22 of the second elongated member 14. A pair of second actuators 34 is illustrated. One of the pair of second actuators 34 is connected to the second actuator connection 24 of the first elongated member 12 and the second of the pair of second actuators 34 is connected to the second actuator connection 24 of the second elongated member 14, such that activation of the pair of first actuators 32 urges pivotal movement of the first and second elongated members 12 and 14 to bring the distal jaw ends 16 closer together and activation of the pair of second actuators 34 urges pivotal movement of the first and second elongated members 12 and 14 to move the distal jaw ends 16 apart.

Distal jaw ends of the first and second elongated members can have various shapes.

Figures 4, 5:
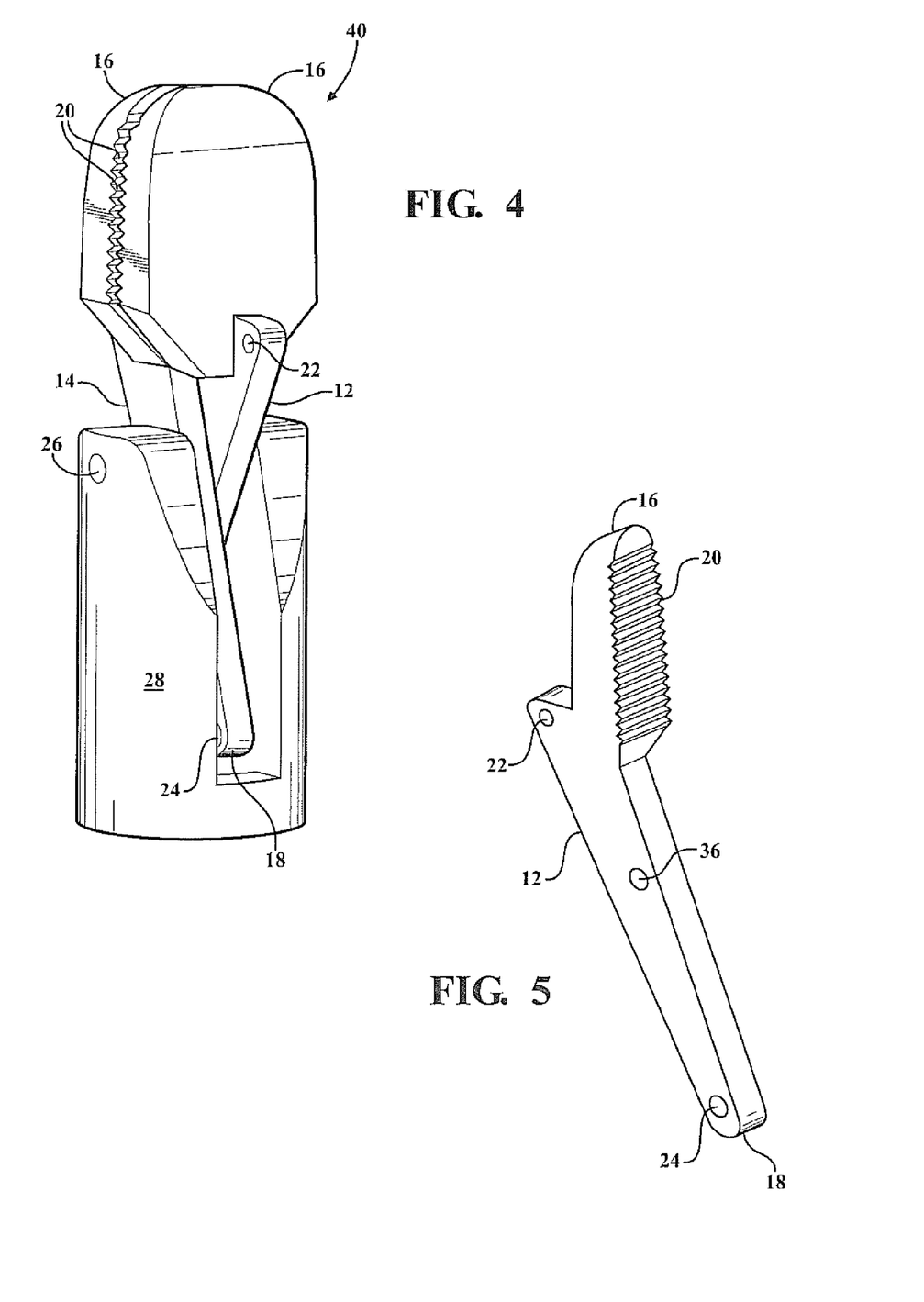
FIG. 4 is a perspective view of a surgical tool according to an embodiment of the present invention.
FIG. 5 is a perspective view of one arm of a surgical tool according to an embodiment of the present invention.

FIG. 4 shows a "wide-jaw" embodiment of a surgical tool of the present invention, 40. The illustrated surgical tool includes pivotally attached first and second elongated members 12 and 14. Each of the first and second elongated members have a distal jaw end 16 and a proximal end 18. The distal jaw ends 16 include opposing gripping surfaces of the jaws 20.

Each of the first and second elongated members 12 and 14 has a connecting pin opening disposed between the distal jaw end 16 and the proximal end 18 for insertion of a connecting pin therethrough. A connecting pin 26 pivotally attaching the first and second elongated members 12 and 14 to a housing 28 is illustrated.

Each of the first and second elongated members 12 and 14 has a first actuator connection 22 disposed between the distal jaw end 16 and the connecting pin opening and a second actuator connection 24 disposed between the proximal end 18 and the connecting pin opening.

FIG. 5 shows a first elongated member 12 having a distal jaw end 16 and a proximal end 18, connecting pin opening 36 disposed between the distal jaw end 16 and the proximal end 18 for insertion of a connecting pin therethrough. A gripping surface of a jaw is illustrated at 20.

The first elongated members 12 has a first actuator connection 22 disposed between the distal jaw end 16 and the connecting pin opening 36 and a second actuator connection 24 disposed between the proximal end 18 and the connecting pin opening 36.

According to embodiments of the present invention, a surgical tool described herein is used through the working channel of an endoscope and is sized accordingly. For example, tool insertion ports on standard endoscopes do not allow long rigid sections to pass through, therefore a surgical tool tip according to embodiments of the present invention has a maximum length of about 10.0 mm. Further aspects of a surgical tool according to embodiments of the present invention include (1) an open jaw-to-jaw angle of 90 degrees, (2) a length of least 5.0 mm from pivot point to tip and (3) at least 3.25 mm of unobstructed external jaw length.

In particular embodiments, a surgical tool of the present invention is used in a 3.3 mm working channel of a flexible endoscope and therefore the outer diameter of the surgical tool has a maximum dimension equal to or less than about 3.0 millimeters.

Particular sizes of surgical tools and/or components of surgical tools according to the present invention described herein are intended as exemplary and are considered non-limiting.

Surgical tools of the present invention are made of any of various materials used in manufacture of surgical tools, including both rigid and flexible materials, exemplified by, but not limited to, surgical steel and flexible plastics.

Any of various well-known methods can be used to manufacture a surgical tool of the present invention, such as wire electrical discharge machining (EDM).

Optionally, methods used to manufacture a surgical tool are those described in U.S. Patent Application Publication 2010/0075170. Briefly described, a manufacturing process described in U.S. Patent Application Publication 2010/0075170 includes a) mold fabrication; b) colloid preparation; c) gel-casting slurry preparation; d) mold infiltration, gel-casting, and planarization; and e) mold removal and sintering. The final parts manufactured according to this method are filtered and cleaned and assembled if necessary.

Surgical tools of the present invention can be used in any of various medical procedures, including, but not limited to MIS and NOTES.

A surgical tool described herein is used in a surgical procedure on a subject, such as, but not limited to, a human. Surgical tools described herein are used in surgical procedures on non-human subjects according to embodiments of the present invention, such as a companion animal including but not limited to dogs and cats; livestock including but not limited to cattle, horses, sheep, goats and poultry; and laboratory animals including but not limited to rodents.

Any patents or publications mentioned in this specification are incorporated herein by reference to the same extent as if each individual publication is specifically and individually indicated to be incorporated by reference.

The devices and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A surgical tool assembly, comprising:
a first elongated member and a second elongated member, each of the first and second elongated members having a proximal end and a distal jaw end, the first and second elongated members pivotally attached to each other at a pivotal attachment, each of the first and second elongated members having a first actuator connection defined between the distal jaw end and the pivotal attachment of the first and second elongated members and a second actuator connection defined between the proximal end of the first and second elongated members and the pivotal attachment of the first and second elongated members;
a pair of first actuators, one of the pair of first actuators connected to the first actuator connection of the first elongated member and the second of the first actuators connected to the first actuator connection of the second elongated member;
a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members only to bring the distal jaw ends closer together and activation of the pair of second actuators urges pivotal movement of the first and second elongated members only to move the distal jaw ends apart; and
a housing supporting the pivotally attached elongated members.

2. The surgical tool assembly of claim 1, further comprising a tool shaft attached to the housing supporting the pivotally attached elongated members.

3. The surgical tool assembly of claim 1, further comprising a controller in operable connection with a pair of first actuators and the pair of second actuators.

4. The surgical tool assembly of claim 1, further comprising a wire in electrical communication with a power source and with the distal jaw end of at least one of the first and second elongated members, the power source operable to deliver an electrical current via the wire to the distal jaw end of at least one of the first and second elongated members.

5. The surgical tool assembly of claim 2, wherein the tool shaft is an articulated tool shaft.

6. A surgical tool assembly, comprising:
   a housing having a first connecting pin opening and a second connecting pin opening;
   a first elongated member and a second elongated member, each of the first and second elongated members having a proximal end, a distal jaw end and a connecting pin opening disposed therebetween for pivotal attachment of the first and second elongated members, each of the first and second elongated members having a first actuator connection defined between the distal end and the connecting pin opening and a second actuator connection defined between the proximal end of the first and second elongated members and the connecting pin opening of the first and second elongated members;
   a connecting pin attaching the first elongated member, second elongated member and the housing;
   a pair of first actuators, one of the pair of first actuators connected to the first actuator connection of the first elongated member and the second of the pair of first actuators connected to the first actuator connection of the second elongated member; and
   a pair of second actuators, one of the pair of second actuators connected to the second actuator connection of the first elongated member and the second of the pair of second actuators connected to the second actuator connection of the second elongated member, such that activation of the pair of first actuators urges pivotal movement of the first and second elongated members only to bring the distal jaw ends closer together and activation of the pair of second actuators urges pivotal movement of the first and second elongated members only to move the distal jaws apart.

7. The surgical tool assembly of claim 6, wherein the housing is attached to a distal functional end of a flexible insertion portion of an endoscopic instrument and/or to a flexible sheath of a flexible insertion portion of an endoscope.

8. The surgical tool assembly of claim 6, wherein the pair of first actuators is a pair of wire actuators.

9. The surgical tool assembly of claim 6, wherein the pair of second actuators is a pair of wire actuators.

10. A surgical procedure, comprising:
    providing a surgical tool according to claim 1;
    inserting the surgical tool into the body of a surgical patient; and
    activating the first pair of actuators to grasp a tissue of the surgical patient and/or activating the second pair of actuators to spread a tissue of the surgical patient.

11. The surgical procedure of claim 10, further comprising:
    delivering and electrical current to the distal jaw end of at least one of the first and second elongated members in contact with a tissue of the surgical patient, thereby cauterizing the tissue of the surgical patient.

* * * * *